# United States Patent [19]

Harvey

[11] 4,362,883
[45] Dec. 7, 1982

[54] PREPARATION OF DIBENZOFURAN

[75] Inventor: Robert J. Harvey, Teaneck, N.J.

[73] Assignee: The Halcon SD Group, Inc., New York, N.Y.

[21] Appl. No.: 315,784

[22] Filed: Oct. 28, 1981

[51] Int. Cl.$^3$ ............................................. C07D 307/91
[52] U.S. Cl. .................................................... 549/460
[58] Field of Search .................... 260/346.71; 549/460

[56] References Cited
PUBLICATIONS

Shiotani et al., J. Chem. Soc., Perkin I (1976), pp. 1236–1241.

*Primary Examiner*—Henry R. Jiles
*Assistant Examiner*—Bernard Dentz
*Attorney, Agent, or Firm*—William C. Long; Riggs T. Stewart; Harold N. Wells

[57] ABSTRACT

Dibenzofuran is prepared by reacting diphenyl ether in an oxygen-containing atmosphere in the presence of a palladium carboxylate catalyst, a carboxlyic acid and a copper carboxylate promoter or co-catalyst.

3 Claims, No Drawings

PREPARATION OF DIBENZOFURAN

This invention relates to the preparation of dibenzofuran and is more particularly concerned with the preparation of this compound from diphenyl ether.

Dibenzofuran, also known as diphenylene oxide, and its derivatives are useful intermediates for the preparation of dyestuffs, stabilizers for organic materials, and other useful chemical products. Further, dibenzofuran is useful as a high boiling solvent for various organic materials. Pope in Chem. Weekbl., 61, 598-600 (1965) discloses that the eutectic mixture of dibenzofuran and biphenyl may be used as a heat-transfer agent.

The general commercial availability of dibenzofuran, however, has involved problems caused by high costs, purity and/or low yields from desirable raw materials, resulting from low selectivity to the desired product of the raw material reacted. Commercially available dibenzofuran, for example, is generally obtained from coal tar and frequently contains impurities such as acenaphthene and fluorene which cannot conveniently be separated by commercially suitable methods such as washing, recrystallization, or distillation. In some cases dibenzofuran having greater purity in comparison with that obtained from coal tar may be produced synthetically but the prior art methods are costly because of expensive starting materials, complicated procedures, low yields or the like. For example, dibenzofuran has been obtained in a 30% yield by Graebe and Ullman, as reported in Ber. 29, 1877 (1896) by diazotization and subsequent hydrolysis of 2-aminodiphenyl oxide. Tauber and Halberstadt describe in Ber. 25, 2745 (1892) a similar treatment of 2,2'-diaminodiphenyl to produce dibenzofuran in 75% yield. These two methods, however, are not readily adapted to commercial operation owing to the high cost and difficulty of obtaining the strating materials required. Hale and Stoesser in U.S. Pat. No. 1,808,349 produce dibenzofuran by the intramolecular dehydrogenation of orthophenylphenol over a refractory oxide catalyst. Cullinane in J. Chem. Soc. 2267 (1930) obtain dibenzofuran in only 20% yield in eight hours by pyrolysis of phenol over litharge at 150° C.

Fishel U.S. Pat. No. 4,009,185 proposes the preparation of dibenzofuran from diphenyl ether, which is also known as diphenyl oxide, by means of a cerium-containing catalyst, preferably in combination with an oxide of another metal. Walsh and Preston (U.S. Pat. No. 3,108,121) also react diphenyl ether and their process calls for the presence of a 5% platinum on charcoal catalyst to obtain dibenzofuran. Shiotani and Itatani (Angew. Chem. 86 478, 1974) use a palladium acetate catalyst to produce dibenzofuran from diphenyl oxide but obtain much dimerized product as well. Itatani et al. U.S. Pat. No. 4,042,603 describes the preparation of substituted dibenzofurans from substituted diphenyl ethers or benzophenones by an oxidative coupling reaction in the presence of a carboxylate salt of palladium or a palladium organic complex and in the presence of a fatty acid ester solvent. Itatani et al., however, do not describe the preparation of unsubstituted dibenzofuran and the examples relating to the formation of the various substituted dibenzofurans show relatively low selectivities with reference to ether reacted.

It is accordingly an object of this invention to provide an improved process for the preparation of dibenzofuran from diphenyl ether in the presence of a palladium catalyst wherein the selectivity to the desired product is significantly improved.

This and other objects are achieved, in accordance with the invention, by a process wherein diphenyl ether is reacted in an oxygen-containing atmosphere in the presence of a palladium carboxylate catalyst and a carboxylic acid solvent, as well as in the presence of a promoter or co-catalyst which is a copper carboxylate, to convert the diphenyl ether with increased selectivity into substantial quantities of dibenzofuran with minimum formation of dimeric or polymeric by-products. It has been surprisingly discovered that the presence of the copper carboxylate has the effect of increasing selectivity in a dramatic manner.

The catalyst employed can be any carboxylic acid salt of palladium, which may be either a fatty acid salt or an aromatic acid salt. Suitable fatty acids salts include the salts of alkanoic acids having 1-20 carbon atoms, preferably 1-4 carbon atoms, such as palladium formate, palladium acetate, palladium propionate, palladium butyrate, palladium valerate, palladium decanoate, and the like. The preferred salt is palladium acetate. Suitable aromatic carboxylic acid salts include palladium benzoate, palladium toluate, and the like.

The amount of palladium carboxylate catalyst is not critical and is not a parameter of the process of the invention and can vary over a wide range. As is well known to persons skilled in the art, the amount of catalyst used is that which will provide a suitable and reasonable reaction rate since reaction rate is influenced by the amount of catalyst. However, essentially any amount of catalyst will facilitate the reaction and can be considered a catalytically-effective quantity. Typically, the amount of catalyst used is 0.1 to 10 wt. %, preferably 0.5 to 5 wt. %.

The carboxylic acid solvent can be any carboxylic acid containing 1-20 carbon atoms such as formic acid, acetic acid, propionic acid, butyric acid, valeric acid, caproic acid, decanoic acid, dodecanoic acid and the like. Preferably, however, the carboxylic acid solvent contains 1-5 carbon atoms, and especially preferred is acetic acid. In general, it is desirable that the carboxylic acid solvent correspond to the carboxylate moiety of the catalyst. The amount of solvent can vary over a wide range and is not a parameter of the process. Ordinarily, enough solvent is used to render the system homogeneous.

The copper carboxylate co-catalyst or promoter can, like the catalyst, be any copper carboxylate having 1-20 carbon atoms, preferably 1-4 carbon atoms, such as the carboxylate moieties named above in connection with the catalyst and, is in the case of the catalyst, the preferred copper carboxylate is copper acetate. Indeed, it is preferred that the copper carboxylate contain the same carboxylate moiety as the catalyst.

The amount of copper carboxylate co-catalyst or promoter is based on the amount of catalyst and can vary widely but generally the copper carboxylate is employed in an amount which is 0.1-10%, preferably 0.5-5%, of the amount of palladium carboxylate catalyst in the system.

As mentioned, the reaction is carried out in an oxygen-containing system and, while the process can be effected at atmospheric pressure, ordinarily the reaction is run at super-atmospheric pressure under an oxygen partial pressure of at least 50 psi, preferably at least 300 psi. The maximum pressure is, of course, dictated by the equipment employed but ordinarily oxygen partial pressures greater than 2,000 psi serve no useful purpose. The oxygen can be employed in pure form or it can be diluted with inert diluents such as nitrogen, carbon dioxide, argon and helium. Ordinarily, the oxygen concentration of the diluted oxygen, when employed, is at least 20%.

The reaction is suitably carried out in the liquid phase and the total pressure should, of course, be sufficient to maintain the diphenyl ether and the dibenzofuran in the liquid phase in the reactor under the temperature employed. The reaction temperature can vary from 25° C. to 250° C. but generally a temperature of at least 100° C., preferably in the range of 120° C. to 140° C. is employed. Temperatures greater than 300° C. appear to serve no useful purpose and merely increase the chance of decomposition of the reactant or the reaction product, or the formation of polymers.

The time of reaction is not a parameter of the process. In order to ensure sufficient conversion of the diphenyl ether, reaction times of 1 to 6 hrs. are preferably employed. It will be understood, however, that the effectiveness of the process will be apparent when lesser or greater reaction times are observed.

The process is, as mentioned, carried out preferably under superatmospheric pressure, and the reaction vessel used should, therefore, be one which is constructed to withstand the applied pressure. Typically, the reaction vessel is an autoclave which may be of the rocking or rotating type or may be provided with an agitator. In carrying out the reaction, the diphenyl ether, the solvent, the catalyst and the copper carboxylate are charged to the reaction vessel which is then sealed and pressured with oxygen or an oxygen-containing gas to the desired oxygen partial pressure. The autoclave is then heated to the selected operating temperature and is maintained at this temperature for the selected reaction time. The temperature and pressure do not, of course, have to be maintained at one specific value but can fluctuate and, if needed, additional amounts of oxygen or oxygen-containing gas can be supplied to provide the operating pressure selected.

At the end of the reaction, the autoclave is allowed to cool to room temperature, excess gas vented and the reaction mixture removed. The liquid components of the reaction mixture are readily separated from the catalyst and promoter by conventional means, such as filtration, and the product dibenzofuran is readily recovered from the liquid, also by conventional means, such as fractional distillation, as will be readily apparent to persons skilled in the art.

The process can be carried out batch-wise as described above, but it is also adapted to be carried out continuously in a system in which the reactants are continuously fed to the reaction vessel and the reaction product is continuously removed. Alternatively, the reactants can be intermittently fed and the reaction product intermittently removed. Apparatus permitting this type of operation is well-known to persons skilled in the art.

In the following examples, the apparatus used was a 130 cc. autoclave provided with magnetic disc agitation. In the examples, all parts are by weight unless otherwise indicated.

It will be, of course, understood that the process of this invention is not limited to any specific manner of operation and that it may be carried out in other ways as will be readily obvious to persons skilled in the art.

The following examples will serve to provide a fuller understanding of the invention, but it is to be understood that these examples are given for illustrative purposes only, and are not to be interpreted as limiting the invention in any way. Analyses of the reaction product mixtures referred to in the Examples were carried out by means of gas chromotography. In the Examples, all parts are by weight, unless otherwise indicated.

EXAMPLE 1

The apparatus described above was charged with 5 parts of diphenyl ether, 45 parts of acetic acid, 0.5 part of palladium acetate and 1 part of cupric acetate, Cu$(C_2H_3O_2)_2.H_2O$, and was pressured to 300 psig with oxygen. The reaction mixture was then heated to 140° C. and maintained at this temperature with stirring for 3 hours. Thereafter, the reactor was cooled, vented, and the reaction mixture filtered to remove the catalyst and promoter. Analysis of the filtered liquid showed that the diphenyl ether had been converted to dibenzofuran with a selectivity of 70%.

COMPARATIVE EXAMPLE A

Example 1 was repeated exactly as described except that the cupric acetate was omitted from the charge. Analysis of the reaction liquid showed that the diphenyl ether had been converted to dibenzofuran with a selectivity of only 42%.

EXAMPLE 2

Example 1 was repeated except that the reaction was carried out for 6 hours. Analysis of the reaction liquid showed that dibenzofuran had been produced with a selectivity of 59%.

COMPARATIVE EXAMPLE B

Example 2 was repeated but the cupric acetate was omitted from the charge. The selectivity fell to 28%.

EXAMPLE 3

Example 1 was again repeated but in this case the amount of cupric acetate was increased to 2 parts and the reaction was run for 6 hours as in Example 2. Analysis showed a selectivity of diphenyl ether to dibenzofuran of 60%.

EXAMPLE 4

The apparatus described above was charged with 10 parts of diphenyl ether, 40 parts of acetic acid, 0.5 part of palladium acetate and 1 part of cupric acetate and was pressured to 300 psig with oxygen. The reaction mixture was then heated to 140° C. and maintained at this temperature with stirring for 3 hours. Thereafter, the reactor was cooled, vented, and the reaction mixture filtered to remove the catalyst and promoter. Analysis of the filtered liquid showed that the diphenyl ether had been converted to dibenzofuran with a selectivity of 62%.

COMPARATIVE EXAMPLE C

Example 4 was repeated with the exception that the 1 part of cupric acetate was omitted. Analysis showed that the selectivity had dropped to 35%.

EXAMPLE 5

The apparatus described above was charged with 2.5 parts of diphenyl ether, 47.5 parts of acetic acid, 0.5 part of palladium acetate and 1 part of cupric acetate and was pressured to 300 psig with oxygen. The reaction mixture was then heated to 140° C. and maintained at this temperature with stirring for 3 hours. Thereafter, the reactor was cooled, vented, and the reaction mixture filtered to remove the catalyst and promoter. Analysis of the filtered liquid showed that the diphenyl ether had been converted to dibenzofuran with a selectivity of 89%.

COMPARATIVE EXAMPLE D

Example 5 was repeated except that the 1 part of cupric acetate was not included in the reaction system. The selectivity was 58%.

What we claim is:

1. A process for producing dibenzofuran which comprises reacting diphenyl ether in the presence of a palladium carboxylate catalyst, a carboxylic acid and a copper carboxylate promoter or co-catalyst.

2. A process as defined in claim 1, wherein the palladium carboxylate is palladium acetate.

3. A process as defined in claim 1, wherein the palladium carboxylate is palladium acetate, the carboxylic acid is acetic acid and the copper carboxylate is a copper acetate.

* * * * *